(12) United States Patent
Santek et al.

(10) Patent No.: US 11,516,437 B2
(45) Date of Patent: Nov. 29, 2022

(54) STEREO MICROSCOPE FOR USE IN MICROSURGICAL OPERATIONS ON A PATIENT AND METHOD FOR CONTROLLING THE STEREO MICROSCOPE

(71) Applicant: BHS Technologies GmbH, Innsbruck (AT)

(72) Inventors: Michael Santek, Goetzens (AT); Gregor Burger, Völs (AT); Mark Capelli, Innsbruck (AT); Markus Friedrich Hütter, Zirl (AT)

(73) Assignee: BHS Technologies GmbH, Innsbruck (AT)

( * ) Notice: Subject to any disclaimer, the term of this patent is extended or adjusted under 35 U.S.C. 154(b) by 0 days.

(21) Appl. No.: 17/041,879

(22) PCT Filed: Mar. 25, 2019

(86) PCT No.: PCT/AT2019/000005
§ 371 (c)(1),
(2) Date: Sep. 25, 2020

(87) PCT Pub. No.: WO2019/183648
PCT Pub. Date: Oct. 3, 2019

(65) Prior Publication Data
US 2021/0014459 A1    Jan. 14, 2021

(30) Foreign Application Priority Data
Mar. 26, 2018 (AT) .................................. A 81/2018

(51) Int. Cl.
*H04N 7/00* (2011.01)
*H04N 7/18* (2006.01)
(Continued)

(52) U.S. Cl.
CPC ............. *H04N 7/181* (2013.01); *A61B 90/20* (2016.02); *G02B 21/0012* (2013.01);
(Continued)

(58) Field of Classification Search
CPC .... H04N 7/181; H04N 13/344; H04N 13/296; H04N 13/239; H04N 5/23299;
(Continued)

(56) References Cited

U.S. PATENT DOCUMENTS 5,347,714 A * 9/1994 Prochaska ............. B26B 21/227
30/32
5,867,210 A * 2/1999 Rod ...................... H04N 13/239
348/51
(Continued)

FOREIGN PATENT DOCUMENTS

DE          60124973 T2    9/2007
DE    102015218926 A1    3/2017
(Continued)

OTHER PUBLICATIONS

International Searching Authority—International Search Report—International Application No. PCT/AT2019/000005 dated Jul. 26, 2019, together with the Written Opinion of the International Searching Authority, 13 pages.

(Continued)

*Primary Examiner* — Frank F Huang
(74) *Attorney, Agent, or Firm* — Sunstein LLP

(57) ABSTRACT

A stereo microscope includes a stand, two optical image acquisition units configured to connect to the stand to capture a stereoscopic image, which define an imaging plane using two optical axes of the image acquisition units, a pair of video glasses including two optical image reproduction units, each having an optical axis and a display for reproducing an image, which together define an image plane, (Continued)

wherein the optical image reproduction units are arranged to produce a stereoscopic image impression, and two optical axes of the optical image reproduction units define an image reproduction plane, a detection device configured to determine spatial orientation of the video glasses, the image reproduction plane, the image plane and the imaging plane, and a control unit configured to pivot the stand so that the intersection lines of the image plane and the imaging plane on the image reproduction plane are made parallel. Methods are also disclosed.

17 Claims, 5 Drawing Sheets

(51) Int. Cl.
*A61B 90/20* (2016.01)
*H04N 13/344* (2018.01)
*H04N 13/296* (2018.01)
*H04N 13/239* (2018.01)
*H04N 5/232* (2006.01)
*G02B 21/00* (2006.01)
*G02B 21/36* (2006.01)
*H04N 5/225* (2006.01)
*H04N 5/247* (2006.01)
*H04N 5/38* (2006.01)
*A61B 34/20* (2016.01)
*A61B 90/25* (2016.01)
*A61B 90/00* (2016.01)
*A61B 90/50* (2016.01)
*G06F 3/04886* (2022.01)

(52) U.S. Cl.
CPC ......... *G02B 21/368* (2013.01); *H04N 5/2253* (2013.01); *H04N 5/23299* (2018.08); *H04N 5/247* (2013.01); *H04N 5/38* (2013.01); *H04N 13/239* (2018.05); *H04N 13/296* (2018.05); *H04N 13/344* (2018.05); *A61B 90/25* (2016.02); *A61B 2034/2048* (2016.02); *A61B 2090/368* (2016.02); *A61B 2090/371* (2016.02); *A61B 2090/373* (2016.02); *A61B 2090/502* (2016.02); *G06F 3/04886* (2013.01)

(58) Field of Classification Search
CPC ........ H04N 5/2253; H04N 5/247; H04N 5/38; A61B 90/20; A61B 2034/2048; A61B 90/25; A61B 2090/368; A61B 2090/371; A61B 2090/373; A61B 2090/502; A61B 90/37; A61B 2090/067; A61B 2034/2055; A61B 2090/372; A61B 34/20; A61B 90/361; G02B 21/0012; G02B 21/368; G02B 27/0179; G02B 7/001; G02B 2027/0134; G02B 21/22; G02B 27/017; G02B 21/365
See application file for complete search history.

(56) References Cited

U.S. PATENT DOCUMENTS

| | | | | |
|---|---|---|---|---|
| 2003/0151810 | A1* | 8/2003 | Haisch | H04N 13/254 359/464 |
| 2005/0063047 | A1* | 3/2005 | Obrebski | G02B 21/24 359/368 |
| 2012/0068913 | A1* | 3/2012 | Bar-Zeev | G02B 27/0172 345/8 |
| 2017/0007351 | A1 | 1/2017 | Yu | |

FOREIGN PATENT DOCUMENTS

| | | |
|---|---|---|
| DE | 102016113593 A1 | 7/2017 |
| EP | 1152275 B1 | 11/2001 |
| EP | 1333306 B1 | 8/2003 |
| WO | 2003002011 A1 | 1/2003 |
| WO | 2017192996 A2 | 11/2017 |

OTHER PUBLICATIONS

Austrian Patent Office—Search Report—Austrian Application No. A 81/2018, dated Sep. 13, 2018, 2 pages.

* cited by examiner

STEREO MICROSCOPE FOR USE IN MICROSURGICAL OPERATIONS ON A PATIENT AND METHOD FOR CONTROLLING THE STEREO MICROSCOPE

CROSS-REFERENCE TO RELATED APPLICATIONS

This application is the national phase entry of International Patent Application No. PCT/AT2019/000005 filed on Mar. 25, 2019, and claims the benefit of Austrian Patent Application No. A 81/2018 filed Mar. 26, 2018, the disclosures of which are incorporated herein by reference in their entirety.

TECHNICAL FIELD

The present invention relates to a stereo microscope for use in microsurgical interventions on the patient and to a method for controlling the stereo microscope.

BACKGROUND OF THE INVENTION

In the field of surgery on the smallest structures, for example in neurosurgery or surgical interventions on the ossicles in the middle ear, as well as in implant surgery, microscope-assisted surgical operation is known. The area to be treated, referred to below as the area of surgical intervention, is shown to the surgeon on the patient at which the microsurgical intervention is to be carried out using a microscope.

From U.S. Pat. No. 8,005,571 B2 a robot system for use in surgical interventions is known. The robot system includes a stereo microscope. With this system, the surgeon sits away from the patient in front of a computer that controls the robot system and stereo microscope. The robot system comprises the surgical tools used for the surgical intervention and arms with which these tools can be moved. The stereo microscope is thus firmly connected to the arms that guide the surgical tools. In this way, the surgeon can always be presented with an image of the engagement area in which the arms move from a predetermined direction, usually from below, into the displayed image area. A disadvantage of such a system is that the surgeon is far away from the patient and thus only has a limited overall impression of the intervention. Another disadvantage of this system is that the arms of the robot system do not allow the surgical tools to be guided as precisely as the hands of the surgeon are able to do.

Another stereomicroscopic system for use in microsurgery is known from US20120190965. The structure of the system is comparable to that of the system known from US8005571B2 and has the same disadvantages. Here too, the fixed connection of the stereo microscope to the arms guiding the surgical tool does not require to establish an eye-hand coordination. It is also disadvantageous here that the arms with the surgical tools can only approach the area of surgical intervention from one side.

It is therefore an object of the present invention to provide a stereo microscope 101 that enables the user 103, i.e. the surgeon, not only to provide a stereoscopic image of the area of surgical area 117, but also that the user 103 can move freely and that from any viewing angle it is continuously ensured that the eye-hand coordination is also guaranteed and corresponds stereoscopically to the natural impression. As a result, the user 103 can carry out the surgery on the enlarged surgery area 117 safely and precisely, and advantageously guide the surgical tool by hand from each side.

SUMMARY OF THE INVENTION

This object is achieved with the stereo microscope according to the invention by the features of claim 1. Advantageous further embodiments are specified in the dependent claims. Claim 15 also specifies a method according to the invention for controlling the stereo microscope according to the invention.

A stereo microscope according the invention for use with microsurgical interventions comprises a stand that can be pivotally connected to a robot arm via a joint, and two with the stand in such a way connectable optical image acquisition units, that a stereoscopic image during use of the surgery area on the patient can be captured and an image acquisition plane defined through the two optical axis of the image acquisition units, a pair of video glasses comprising two optical image reproduction units each having an optical axis and a display for reproducing an image, which together define an image plane, wherein the optical image reproduction units are arranged to produce a stereoscopic image impression with the video glasses to the user wearing the video glasses, and by means of the two optical axis of the optical image reproduction units an image reproduction plane define. A detection device for determining the spatial orientation of the video glasses, image reproduction plane, image plane and image acquisition plane. A control unit adapted to provide a control signal for pivoting the stand such that the intersection lines in the image reproduction plane of the image plane and the image acquisition plane can be made parallel.

The control signal can be optically overlaid in at least one image reproduction unit and adapted for displaying to the user the manual pivoting of the stand around the joint. In a further embodiment, the stand is pivotable about the joint with a motor unit and the control signal is adapted to control the motor unit. In a further embodiment, the two image reproduction units comprise a common display, the display area of which is divided into two halves in order to be able to display one image each to one eye of the user wearing the video glasses.

In an advantageous development, the detection device for determining the spatial orientation of the video glasses and/or image recording plane comprises an optical object detection system or an orientation sensor that can be connected to the video glasses. The orientation sensor is preferably selected from the group tilting sensor, position sensor, acceleration sensor or an inertial measuring system. The stereo microscope according to the invention can in addition comprise a communication unit adapted for real time transfer of the stereoscopic acquired images of the image acquisition unit to the image reproduction unit for stereoscopic displaying. The time delay in the real-time communication is less than 50 milliseconds. The communication unit is adapted to transfer the images through wireless communication.

In an advantageous embodiment, the stand comprises a quick-release plate with which the image acquisition units are connectable. In a further advantageous embodiment, the image acquisition units are movable relative to one another in order to stereoscopically image the surgery area depending on the magnification and/or the distance of the image acquisition units from the surgery area and/or the user's pupillary distance. For this purpose, the image acquisition units may be rotatable in the image acquisition plane, so that the optical axes form an angle of less than 180° to one another. Or adjust the distance of the two image acquisition units from one another depending on the distance of the image acquisition units from the surgery area.

The method according to the invention for controlling a stereo microscope according to the invention comprises a control unit which is adapted to carry out the following steps: detection of the orientation of the video glasses, image reproduction plane and image plane; detecting the orientation of the image acquisition plane; determining a first intersection line from the image plane in the image reproduction plane; determining a second intersection line of the image acquisition plane in the image reproduction plane; determining and output of the determined control signal for pivoting the stand, so that the first and second intersection lines can be brought in parallel.

DESCRIPTION OF THE PREFERRED EMBODIMENTS USING THE PICTURES

In the following, preferred embodiments of the stereo microscope 100 according to the invention for use in microsurgical operations and a method for controlling the stereo microscope according to the invention are described with the aid of the attached figures.

Figure 1:
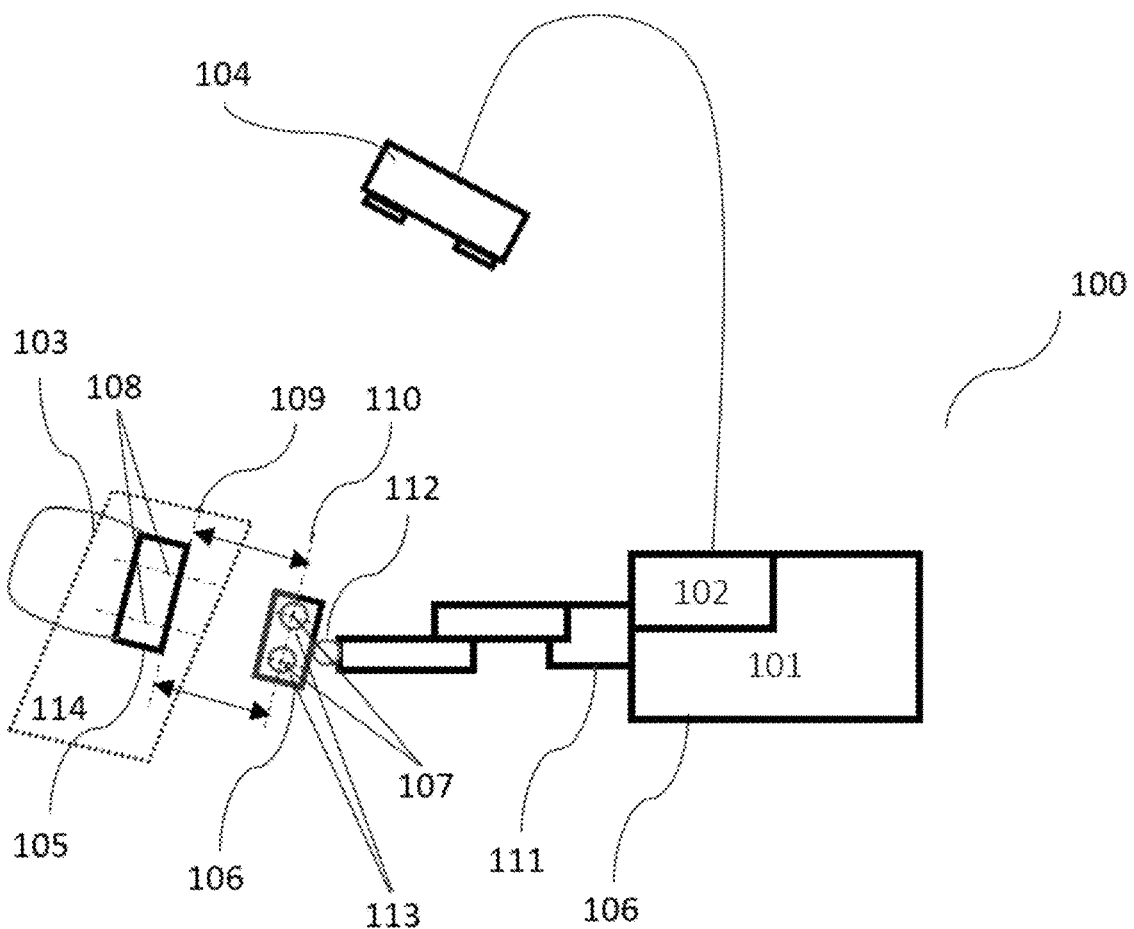
FIG. 1 shows a microsurgical stereo microscope in a preferred embodiment according to the invention.

FIG. 1 shows schematically the structure of an inventive top view stereo microscope 100 for use in microsurgery. The stereo microscope 100 comprises a stand 106 which can be pivotally connected to a robot arm 111 using a joint 112. The robot arm 111 can be fixed in a stable manner on the floor of the operating room via a holding device 106 to avoid vibrations as much as possible. With the stand 106, two optical image acquisition units 113 can be connectable in such a way that a stereoscopic image of the surgery area 117 on the patient to be imaged during use can be captured and through the two optical axes 107 of the image acquisition units 113 defining an image acquisition plane 110. The image acquisition units 113 are adapted to enable an optical magnification of up to 100 times. In an advantageous embodiment, the image acquisition units 113 can additionally be adapted to enable an optical reduction. This is particularly advantageous for the user 103, since he can get an overview over the surgery area 117 and beyond. It also helps the user 103 to orient himself when he approaches the surgery area 117 with the surgical tools in his hands.

In an exemplary embodiment, the two optical image acquisition units 113 can be formed from two objectives, each with a digital image acquisition system, such as a CCD camera. Such image acquisition units 113 are known from the prior art and each have, in a known manner, an optical axis 107 along the objective and running through the rotationally symmetrical centre of the objective lens. The two optical axes 107 run in FIG. 1 into the image plane and the not shown surgery area 117 in the top view is located under the two image acquisition units 113. The two optical axes 107 lie in one plane, the image acquisition plane 110, which is perpendicular to the image plane in FIG. 1 and is shown as a line, the line of intersection of the image acquisition plane 110 with the image plane of FIG. 1. The images captured by the two image acquisition units 113 will, using video glasses 105 comprising two optical image display units 115, each with an optical axis 108 and a display for displaying an image, which together define an image plane 109, be transmitted and displayed to a user 103 wearing the video glasses 105. One image display unit 115 each provides an image for one eye of the user 103. The captured image of one of the two image acquisition units 107 is thus displayed by one of the two image display units 115. It is thereby achieved that the stereoscopically captured image of the surgical area 117 is displayed to each eye of the user 103 wearing the video glasses 105 and the user 103 can be given a stereoscopic image impression of the surgery area 117. A significant advantage of the stereo microscope 100 according to the invention over that known from the prior art is that the user 103 can move freely and perform the surgery from any direction and with any head posture using microsurgical tools guided by the hands of the user 103 at the surgery area 117. However, binocular vision of the human being is far more complex and it is not sufficient to provide only a stereoscopic image impression, especially if through the stereoscopic image impression a natural eye-hand coordination for the user 103 in addition has to be obtained. Correct implementation of the eye-hand coordination is essential for microsurgical interventions, because only a very slight misdirection of the surgical tools guided with the hands of the user 103 can cause serious injuries in the surgery area 117 and subsequently complications on the patient.

For this purpose, the stereo microscope 100 according to the invention comprises in addition a detection device 104 for determining the spatial orientation of the video glasses 105, image reproduction plane 114, image plane 109 and the image acquisition plane 110. The control unit 101 is adapted to provide a control signal for pivoting the stand 106 so that the intersection lines in the image reproduction plane 114 by the image plane 109 and the image acquisition plane 110 can be brought in parallel. This makes it possible for the user 103 not only to provide a stereoscopic image of the surgery area 117, the user 103 can also move freely and it is continuously ensured that the eye-hand coordination also corresponds stereoscopically to the natural impression. As a result, the user 103 can carry out the intervention on the enlarged surgery area 117 safely and precisely. The stereo microscope 100 according the invention can have different modes of movement. For example, in a movement mode, the image acquisition plane 110 can be rotated around the focal point (reference point) in the surgery area 117 when the user 103 wearing the video glasses 105 rotates his head. The stereo microscope 100 according to the invention works with all possible movement modes and associated freely definable reference points and is in no way restricted in any way.

For the detection device 104, any device known from the prior art can be used that is suitable to determine the spatial orientation and position of objects. In a preferred embodiment, the detection device 104 comprises an optical system that, for example, first determines the spatial orientation of the video glasses 105 by means of markings made at previously known points on the video glasses 105. The markings can, for example, be coloured or in the infrared range reflective points, lines or other symbols recognizable by image recognition. The spatial orientation of the image reproduction plane 114 and the image plane 109, the position of which relative to the video glasses 105 is previously known, can then be determined using conventional linear transformation matrices from the spatial orientation of the video glasses 105. This functionality of the detection device 104 can be part of the control unit 101, which in this case is adapted to determine the spatial orientation of the image reproduction plane 114 from the spatial orientation of the video glasses 105. In this way, the computing power of the control unit 101 can advantageously be used for the calculation of the transformation and the detection device 104 is thereby simplified. To do this, the recorded spatial orientation of the video glasses 105 is transmitted in real time to the control unit 101. The transmission can take place with the communication unit 102 or another communication unit not shown in FIG. 1. In a preferred embodiment, communication takes place by radio transmission, which has the advantage that no cable has to be laid in the operating room to the detection device 104. The spatial orientation of the image acquisition plane 110 can be determined via the position information of the robot arm 111 and the relative orientation of the stand 106 to the robot arm 111. The relative orientation of the stand 106 can be determined, for example, with a rotation angle sensor in joint 112. In an analogous manner to before, the spatial orientation of the image acquisition plane 110 can be determined from the orientation information of the robot arm 111 and stand 106 by means of linear transformation matrices. As before, this functionality of the detection device 104 can be part of the control unit 101, which in this case is adapted to determine the spatial orientation of the image acquisition plane 110 from the position of the robot arm 11 and the stand 106. In an alternative embodiment, the optical system of the detection device 104 can by markings on the stand 106 determine the orientation of the stand 106 and from it in an analogous manner as previously described for the video glasses 105 by means of transformation determine the orientation of the image acquisition plane 110.

Figure 2:
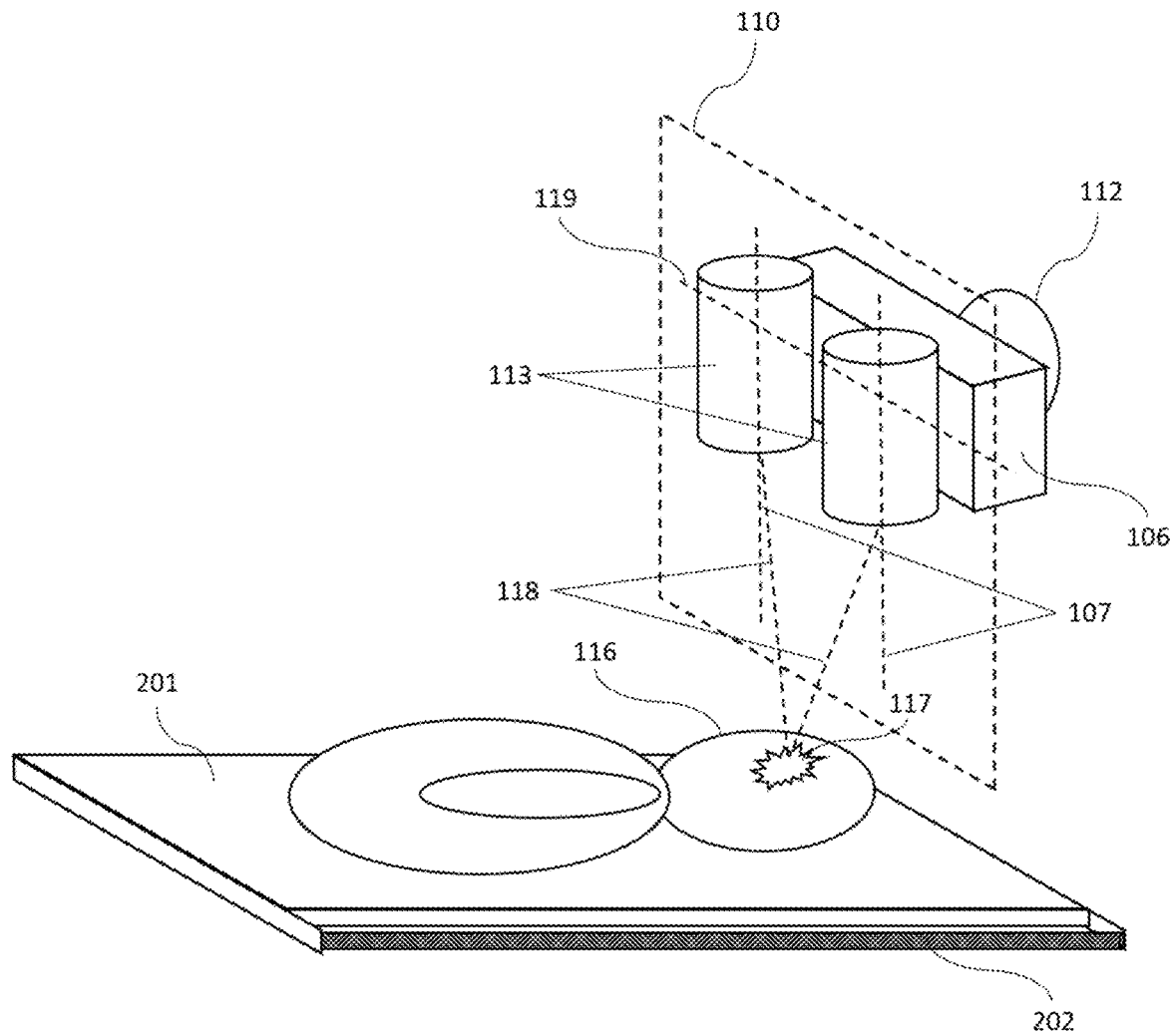
FIG. 2 shows a preferred embodiment of the stand for the stereo microscope according to the invention.

FIG. 2 shows a preferred embodiment of the stand 106 for the stereo microscope 100 according to the invention. The associated optical axes 107 are likewise parallel to one another due to the parallel image recording units 113. This makes it possible for the surgery area 117 to be imaged on patient 116 to be imaged from two different directions 118 with the image acquisition units 113. This image acquisition, which is modelled on human binocular vision, makes it possible to generate a stereoscopic image impression, with which additional depth information can be made available to the user 103. This additional information is essential in microsurgery and enables much safer microsurgery than would otherwise be possible with a binocular microscope. The two optical axes 107 are shown in parallel in FIG. 1, that is for the invention. However, stereo microscope 100 is not required. Any position of the image acquisition units 113 and thus of the optical axes 107 relative to one another is possible as long as the optical axes 107 form an image acquisition plane 110.

In a further advantageous embodiment, the optical axes 107 can be adapted to the eye distance of the user 103. For this purpose, the stand 106 is provided with guide rails along the longitudinal axis 119 of the stand 106. The two image acquisition units 113 can be displaced relative to one another along the guide rail. In an advantageous embodiment of the stereo microscope 100 according the invention, the image acquisition units 113 on the stand 106 can be displaced along the guide rail such that each of the two image acquisition units 113 is at the same distance from the centre point along the longitudinal axis of the guide rail at all times. This has the advantage that the stereoscopically acquired image of the surgery area 117 does not move when the image acquisition units 113 are moved, only the viewing angle and thus the depth information changes with respect to the user 103. In a further advantageous embodiment, the two image acquisition units 113 are connected to racks movable along the guide rail, the racks being arranged such that the teeth engage in a gearwheel located in the centre of the guide rail and move in opposite directions to one another when the gearwheel rotates. It is thereby advantageously achieved that both image acquisition units 113 can be moved relative to one another at the same time with only one motor connected to the gearwheel, and thus the distance between the image acquisition units 113 can be changed. In a further advantageous embodiment, the image acquisition units 113 can be rotated in the image acquisition plane 110. The two movements of the image acquisition units 113, i.e. the movement along the guide rail and the rotary movement in the image acquisition plane 110, can also be combined. For this purpose, the image acquisition units 113 are connected to the stand 106 in such a manner that they can move relative to one another in order to stereoscopically depict the surgery area 117 as a function of the magnification and/or the distance of the image acquisition units 113 from the surgery area 117 and/or the eye distance of the user 103. This means that for every operating position, i.e. magnification, distance of image acquisition units 113 from the surgery area 117, eye distance of the user 103, illumination and enlargement/ reduction the optimum depth of field and thus depth information are ensured in the stereoscopic image acquisition. The movable image acquisition units 113 can be moved manually with a suitable control signal, provided by the control unit 101 to the user 103, for example by means of information overlaid in the video glasses 105. This embodiment is described in more detail with reference to FIG. 5 below. Alternatively, the control unit 101 provides a control signal for activating a motor unit, so that the image acquisition units 113 can be moved and aligned automatically.

The stand 106 can be pivotally connected to a robot arm 111 via a joint 112. This allows the stand 106 with its sensitive image acquisition units 113 for the transport of heavy and unwieldy robot arm 111 can be separated. The robot arm 111 can be attached to a holding device for transport. In a further preferred embodiment, the holding device can comprise a trolley which can be moved to the operation operating table 201 and as close as possible to the area of surgery area 117 on the patient 116. The trolley positioned in this way can also use fold-out or pull-out feet for additional support. In an alternative embodiment, the trolley can also be lowered so that the surface of the trolley floor rests flatly stable on the floor of the operating room. A suitable device for lowering and lifting is, for example, a manually, hydraulically, pneumatically or electrically driven scissor lifting device. Other equivalent and known embodiments are also possible. In a further embodiment, the holder device can have C-shaped clamps for hanging and fixing to the fastening strips 202 running laterally along the operating table 201. By positioning close to the surgery area 117, short arm lengths of the robot arm 111 can be realized, with the particular advantage of increased vibration resistance. The robot arm 111 can be a conventional industrial robot arm which is modified in such a way that the high demands on the positioning accuracy and vibration resistance can be met. Vibration resistance in particular is an important criterion, because even the smallest vibrations appear in the enlarged image of the surgery area 117 also enlarged and lead to unusable blurred images for the user 103. In order to achieve particularly high stability and vibration resistance, the weight ratio of the holding device to the robot arm 111 together with the joint 112, stand 106 and image acquisition units 113 is greater than 2 to 1 in a preferred embodiment.

Figure 3:
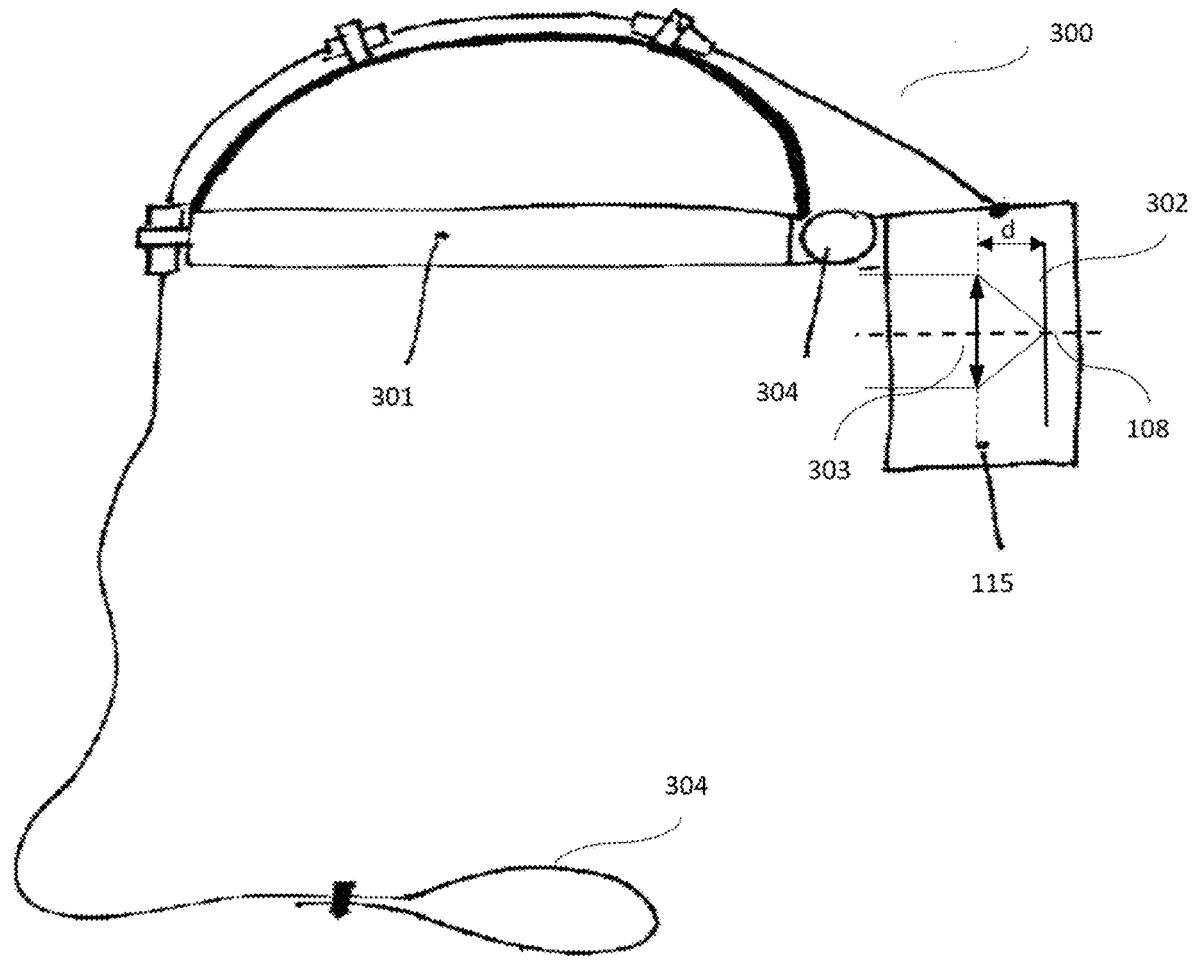
FIG. 3 shows video glasses in one for the invention stereo microscope preferred embodiment.

FIG. 3 shows video glasses 300 with a support device 301 for holding the video glasses 300 on the head of the user 103. The image display units 115 are connected to the support device 301 via a joint 304. The video glasses 300 additionally comprise a cable pull 304 with which the image display unit 115 can be pivoted with the joint upwards out of the field of vision of the user 103 wearing the video glasses. In the following, the video glasses 300 are described only to the extent necessary for understanding the present invention and any video glasses 300 known from the prior art with the features described below or features equivalent thereto can be used with the stereo microscope 100 according to the invention, for example the video glasses 300 which are the subject of another pending national Austrian Patent application of the inventors with the publication number AT 519845. Each image display unit 115 comprises a display 302 and a converging lens 303. The two image display devices 302 of the two image display units are arranged in one plane, forming the image plane 109, and can either be designed as a single display, the image output on the display being divided for each image display unit 115, or as two separate displays. The converging lens 303 is approximately by the focal length d spaced apart in the direction of the optical axis 108 from the image plane 109. In a known manner, this enables imaging in the human eye when the eye is relaxed and focused on infinity. In one embodiment, the image display unit 115 is configured to be adaptable to the eye distance of the user 103 by matching the optical axes 108 with the optical axes of the eyes of the user 103 when the user 103 looks straight ahead and focuses the eyes at infinity. In one embodiment, this is accomplished by moving the image display units 115 to each another. In a further advantageous embodiment, this is implemented in the video glasses 300 without further mechanical elements by shifting the image output of the image display units 115 in the image plane 109 relative to one another. This is done e.g. through the image output by the display and the image to be output is shifted by one or more pixels.

Figure 4:
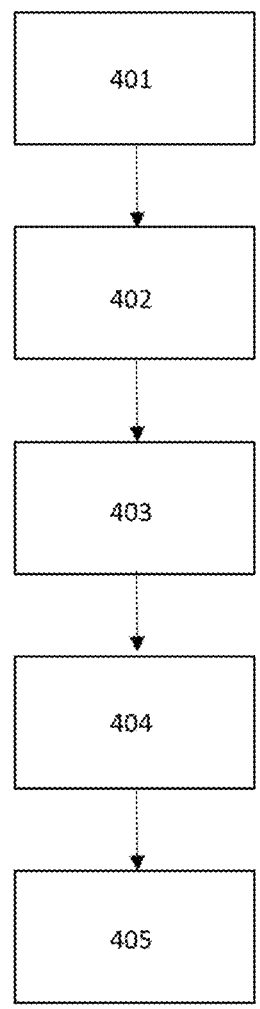
FIG. 4 shows a flow chart for controlling the stereo microscope according to the invention.

FIG. 4 shows a flow chart for controlling the stereo microscope 100 according to the invention. To start up the stereo microscope 100, the stereo microscope 100 is first brought up to the operating table 201 with the trolley and stably placed on the floor of the operating room using the devices described above. Then the stand 106 with the two image acquisition units 113 is positioned over the surgery area 117 to be observed with the robot arm 111. For this purpose, the robot arm 111 is controlled with the control unit 101. The communication unit 102 communicates the images of the surgery area 117 captured by the two image acquisition units 113 in real time to the image display units 115 stereoscopic display. The captured images from each of the two image acquisition units 113 is transmitted to each of the two image display units 115 for display. It is thereby achieved, that the stereoscopically acquired image of the surgery area 117 is displayed to each eye of the user 103 wearing the video glasses 105 and to the user 103 a stereoscopic image impression of the surgery area 117 can be displayed.

For controlling according the invention the stereo microscope 100 according to the invention the control unit 101 is adapted to carry out the steps which are explained in more detail below with reference to FIG. 4. In step 401, the orientation of the image reproduction plane 114 and the image plane 119 is recorded. This can be done with the previously described methods and devices, for example with the aid of the detection device 104 and supply to the control unit 101 for further processing. The orientation of the image reproduction plane 114 can then, for example, by a plane equation of the form E1: $a_1 \cdot x = d_1$ represented, with the three-dimensional vectors $a_1$ and x, as well as the scalar $d_1$ and where "·" denotes the vectorial scalar product. The orientation detected in this way by the detection device 104 can be transmitted, for example, to the control unit 101 using the communication unit 102. In the same way, image plane 109 can be represented by plane equation E: $a \cdot x = d$. In step 402, the orientation of image acquisition plane 119 is detected. As before, the plane equation can be represented by E2: $a_2 \cdot x = d_2$. In step 403, the control unit 101 determines a first cut line from the image plane 109 in the image reproduction plane 114. For this purpose, control unit 101 calculates, for example, the vector product of O1: $a_1 \times a$. It is not necessary to compute the intersection line equation completely, the direction vector O1 calculated by the vector product is sufficient. In step 404, the control unit 101 determines a second intersection line from the image acquisition plane 110 in the image reproduction plane 114. This can be calculated in the control unit 101, for example in the same way as before, by forming the vector product of O2: $a_2 \times a$. Again it is sufficient to calculate the direction vector O2, a complete calculation of the line equation is not necessary. Finally, the control signal for pivoting the stand 106 can be determined and output by the control unit 101 in step 405, so that the first and second intersection lines can be brought in parallel. The control signal could be, for example, an angle information α and a rotation plane D. The control unit 101 could calculate the angle of rotation α, for example, by forming the dot product from the previously determined direction vectors O1 and O2: $\alpha = \arccos(O_1 \cdot O_2 / (|O_1| \cdot |O_2|))$. The control unit 101 can calculate the rotation plane D, for example, from the vector product of the previously determined direction vectors O1 and O2: D: $(O_1 \times O_2) \cdot x = (O_1 \times O_2) \cdot \overline{OP}$, where $\overline{OP}$ denotes the coordinates of the pivot point in the joint 112 around which the stand 106 can be pivoted. The control signal calculated in this way can, as described above, be provided by control unit 101 in such a way by overlaying it into at least one image display unit 115 in order to display to user 103 the manual pivoting of the stand 106. In a further preferred embodiment, the control signal can be provided in order to control a motor unit, which pivots the stand 106 in the calculated rotation plane D by the rotation angle α. For execution of steps 401 to 405, the control unit 101 can be designed as a computer.

Figure 5:
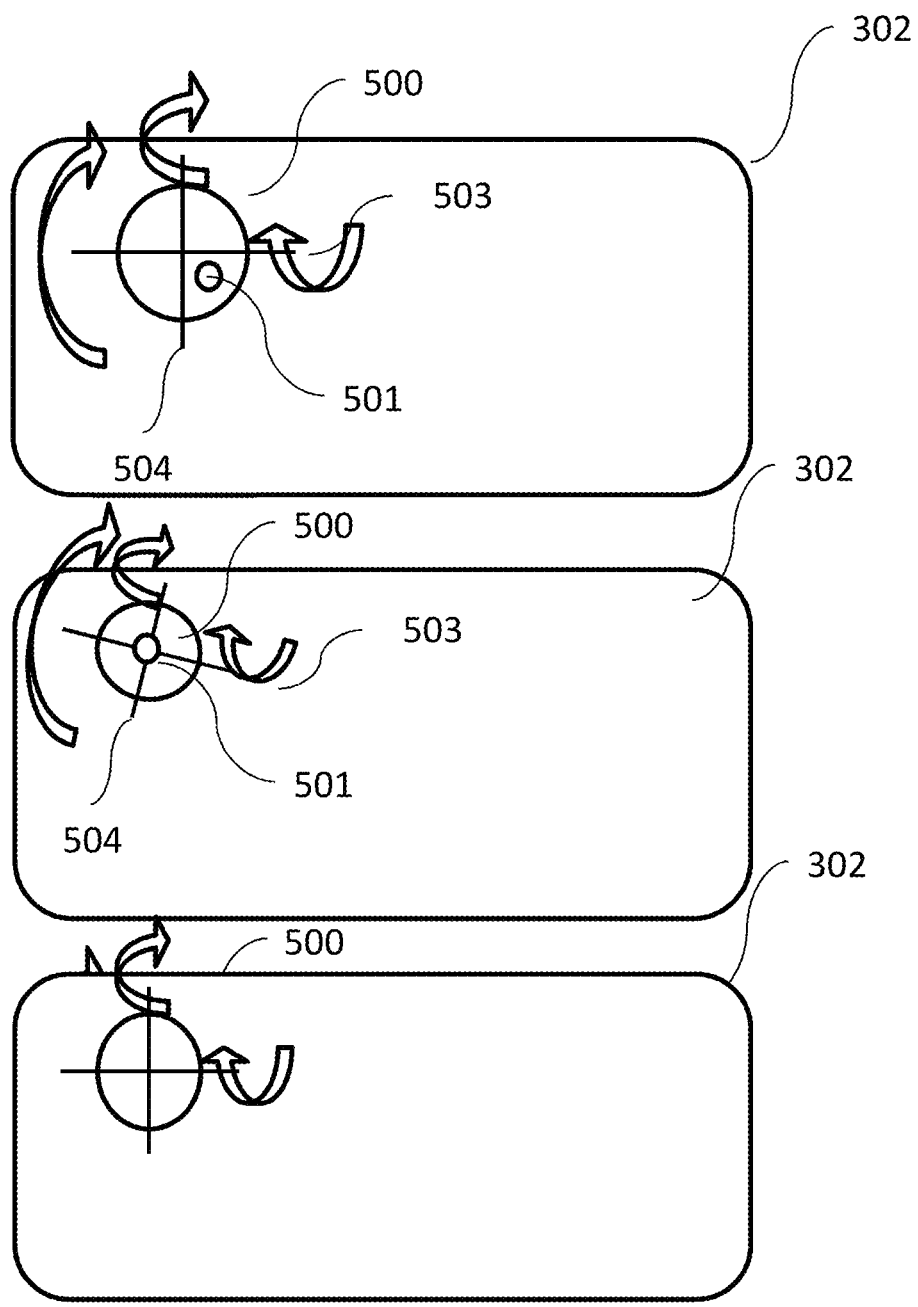
FIG. 5 shows schematically the display of an image reproduction unit with the overlay by an exemplary control signal to show the user the manual pivoting of the stand.

FIG. 5 schematically shows the display 302 of an image display unit 115 with the overlay by an exemplary control signal in order to show the user the manual pivoting of the stand. The optical display of the control signal 500, overlays for example the image area in the upper left corner. It comprises an axis 503 shown horizontally in FIG. 5 and a vertical axis 504 which are perpendicular to one another and form a cross. Point 501 indicates the current relative orientation of the stand 106. If point 501 is below the horizontal axis 503, it is shown to the user that a rotation about the longitudinal axis (X-axis) of the stand 106 is to be carried out as with the double arrow on the horizontal axis 503 and until point 501 on the horizontal axis 503 comes to rest, then stand 106 is aligned along the longitudinal axis, indicated by axis 503. If point 503 is above axis 503, rotation about the longitudinal axis (X axis) is to be carried out by user 103 in the opposite direction. In the same way, stand 106 can be aligned along axis 504, with rotation about the transverse axis (Y axis) of stand 106 having to be carried out here. The third angle of rotation about the vertical axis (Z axis) of the stand 106 can be displayed to the user 103 by rotating the entire cross, formed from the two axes 503 and 504, as shown, for example, in the middle schematic illustration in FIG. 5. Only when axis 503 appears horizontal to user 103, stand 106 is also aligned with the vertical axis of stand 106. Such complete alignment of the stand 106 is shown in the lower figure.

The invention claimed is:

1. Stereo microscope for use in microsurgical surgeries comprising:
  a stand pivotally connectable through a joint to a robot arm,
  two optical image acquisition units configured to connect to the stand in such a way that a stereoscopic image of a surgery area is captured during use on a patient and an image acquisition plane is defined through two optical axes of the optical image acquisition units,
  a pair of video glasses comprising two optical image reproduction units each having an optical axis and a display for reproducing an image, which together define an image plane,
  wherein the optical image reproduction units are arranged to produce a stereoscopic image impression for a user wearing the video glasses, and two optical axes of the optical image reproduction units define an image reproduction plane,
  a detection device configured to determine spatial orientation of the video glasses, the image reproduction plane, the image plane and the image acquisition plane, and
  a control unit adapted to provide a control signal for pivoting the stand by:
    determining a first intersection line from the image plane in the image reproduction plane;
    determining a second intersection line of the image acquisition plane in the image reproduction plane; and
    determining an output of the control signal for pivoting the stand, so that the first and second intersection lines are brought parallel,
  such that the microscope is configured to allow the user to perform the surgery from any direction and with any head posture and to continuously ensure that an eye-hand coordination of the user corresponds stereoscopically to a natural eye-hand coordination.

2. Stereo microscope according to claim 1, wherein the control signal is optically overlaid in at least one image reproduction unit and adapted for displaying to the user manual pivoting of the stand around the joint.

3. Stereo microscope according to claim 1, wherein the stand is pivoted with a motor unit around the joint and the control signal is adapted to control the motor unit.

4. Stereo microscope according to claim 1, wherein the two image reproduction units comprise a common display, the display area of which is divided into two halves in order to be able to display one image each to one eye of the user wearing the video glasses.

5. Stereo microscope according to claim 1, wherein the detection device configured to determine the spatial orientation of the video glasses and/or image acquisition plane comprises an optical object detection system.

6. Stereo microscope according to claim 1, wherein the detection device configured to determine the spatial orientation of the video glasses comprises an orientation sensor connectable to the video glasses.

7. Stereo microscope according to claim 6, wherein the orientation sensor is a tilting sensor, a position sensor, an accelerometer sensor or an inertial measurement system.

8. Stereo microscope according to claim 1, further comprising a communication unit, adapted for real time transfer of the stereoscopic acquired images of the image acquisition unit to the image reproduction unit for stereoscopic displaying.

9. Stereo microscope according to claim 8, wherein the real time transfer includes a time delay less than 50 milliseconds.

10. Stereo microscope according to claim 8, wherein the communication unit is adapted to transfer the images through wireless communication.

11. Stereo microscope according to claim 1, wherein the stand comprises a quick-release plate with which the image acquisition units are connectable.

12. Stereo microscope according to claim 1, wherein the image acquisition units are movable relative to one another in order to stereoscopically image the surgery area depending on magnification and/or distance of the image acquisition units from the surgery area and/or a pupillary distance of the user.

13. Stereo microscope according to claim 12, wherein the image acquisition units are rotatable in the image acquisition plane, so that the optical axes form an angle of less than 180° to one another.

14. Stereo microscope according to claim 12, wherein the distance between the two image acquisition units from one another is dependent on the distance of the image acquisition units from the surgery area.

15. Method for controlling a stereo microscope according to claim 1, wherein the control unit is further adapted to carry out the following steps:
  detecting the orientation of the video glasses, the image reproduction plane and the image plane; and
  detecting the orientation of the image acquisition plane.

16. Stereo microscope according to claim 9, wherein the communication unit is adapted to transfer the images through wireless communication.

17. Stereo microscope according to claim 13, wherein the distance between the two image acquisition units from one another is dependent on the distance of the image acquisition units from the surgery area.

* * * * *